United States Patent
Khamizov et al.

(10) Patent No.: US 7,271,895 B2
(45) Date of Patent: Sep. 18, 2007

(54) FLUORESCENT SENSOR ON BASIS OF MULTICHANNEL STRUCTURES

(75) Inventors: Ruslan Kh. Khamizov, Moscow (RU); Muradin A. Kumakhov, Moscow (RU); Svetlana V. Nikitina, Moscow (RU); Victor A. Mikhin, Maisky (RU); Tatiana I. Zhiguleva, Moscow (RU); Nikolai O. Avotynsh, Moscow region (RU)

(73) Assignee: Institute For Roentgen Optics, Moscow (RU)

( * ) Notice: Subject to any disclaimer, the term of this patent is extended or adjusted under 35 U.S.C. 154(b) by 427 days.

(21) Appl. No.: 11/013,387

(22) Filed: Dec. 17, 2004

(65) Prior Publication Data

US 2005/0225756 A1    Oct. 13, 2005

(30) Foreign Application Priority Data

Apr. 9, 2004    (RU) .............................. 2004110692

(51) Int. Cl.
*G01N 21/01*    (2006.01)
*G01N 1/10*    (2006.01)

(52) U.S. Cl. ...................................... 356/246; 356/244
(58) Field of Classification Search ................ 204/452, 204/601–603; 356/318, 246; 435/6
See application file for complete search history.

(56) References Cited

U.S. PATENT DOCUMENTS

| | | | |
|---|---|---|---|
| 5,192,869 A | | 3/1993 | Kumakhov |
| 5,498,324 A | * | 3/1996 | Yeung et al. ................ 204/452 |
| 5,730,850 A | * | 3/1998 | Kambara et al. ............ 204/603 |
| 5,741,411 A | * | 4/1998 | Yeung et al. ................ 204/452 |
| 5,741,412 A | * | 4/1998 | Dovichi et al. ............. 204/602 |
| 6,017,765 A | * | 1/2000 | Yamada et al. ............ 623/1.15 |
| 6,023,540 A | | 2/2000 | Walt et al. |
| 6,387,236 B2 | * | 5/2002 | Nordman et al. ........... 204/601 |
| 2001/0041339 A1 | * | 11/2001 | Anderson et al. .............. 435/6 |
| 2004/0096960 A1 | * | 5/2004 | Burd Mehta et al. .... 435/287.2 |

FOREIGN PATENT DOCUMENTS

DE        44 11 330        8/2003

(Continued)

OTHER PUBLICATIONS

G.K.Budnikov, What is chemical sensors // Soros Educational Journal, 1988, No. 3, p. 72-76 (in Russian).

(Continued)

*Primary Examiner*—Layla G. Lauchman
*Assistant Examiner*—Jarreas Underwood
(74) *Attorney, Agent, or Firm*—McDermott Will & Emery LLP

(57)    ABSTRACT

Sensor for use in highly sensitive analytical devices for qualitative and quantitative analysis of natural waters and technology-related solutions, containing low concentrations of components determined. Design of a sensor provides for simplification and costs reduction of its manufacture, widening range of solutions analyzed, improvement of their kinetic characteristics and increase in analysis sensitivity. Sensor has multichannel structure in a form of a piece 1 of a polycapillary tube with through capillaries forming microchannels filled up with two layers of immiscible substances. One layer (4) is formed of water or aqueous solution, and another layer (3) is formed of organic substance. The first of the layers in microchannels contains sorbent microgranules 5.

30 Claims, 10 Drawing Sheets

FIG. 1

FOREIGN PATENT DOCUMENTS

| RU | 2096353 | 11/1997 |
| RU | 2157385 | 10/2000 |
| RU | 31859 | 8/2003 |

OTHER PUBLICATIONS

Fluorescent Chemosensors for Ion and Molecule Recognition, ACS Symp. Ser. / ed. A.W.Czarnik // AChS Publ., Washington, DC 1992, 225 p.

V.Barskij, A.Kolchinskij, Yu.Lysov, A.Mirzabekov, Biological microchips containing nucleic acids, proteins and other compounds immobilized in hydrogel: properties and applications in genomics // Molekulyarnaya Biologiya (Molecular Biology), 2002, T.36, p. 563-584 (in Russian).

S.Ampuero, J.O.Bosset, The electronic nose applied to dairy products: a review // Sensors and Actuators B: Chemical, 2003, V.94, p. 1-12.

Seitz W.R., Fiber optic sensors // Anal. Chem., 1984, V.86, No. 1, p. 16-25.

A.S.Scherbakov, S.M.Cheremisin, V.V.Danichev, V.S.Ozerov, Focus-1 X ray fluorescent spectrometer, Proceed. SPIE, 2000, V.4155, p. 131-137.

V.A.Arkad'ev, A.P.Kolomijtsev, M.A.Kumakhov, I.Yu.Ponomarev, I.A.Khodeev, Yu.P.Chertov, I.M.Shakhparonov. Wide-band X ray optics with a large angular aperture. Uspekhi Fizicheskikh Nauk (Advances in Physical Sciences), Mar. 1989 r., V.157, Issue 3, p. 529-537 (in Russian).

\* cited by examiner

FLUORESCENT SENSOR ON BASIS OF MULTICHANNEL STRUCTURES

FIELD OF THE INVENTION

The invention relates to the field of chemical and biological analysis and may be used for development of highly sensitive analytical devices for qualitative and quantitative analysis of aqueous and organic solutions, namely, natural waters and technology-related solutions containing low concentrations of inorganic and organic components being determined, as well as solutions containing biologically active compounds.

BACKGROUND ART

Chemical and biological sensors [1-5] are sensing elements providing direct information on ion or molecular composition of the medium (solution) the sensor is immersed in, without its sampling and preconditioning for analysis. Sensors are used in combination with any analytical registering device. To be used for determination of microcomponents in solutions, the sensors should possess ability for selective adsorption (sorption) of components being determined from these solutions, as well as ability to accumulate these components to concentrations exceeding the detection limits of the registering analytical device. If it is necessary to provide for routine monitoring (tracking the changes in microcomponents concentrations) of water stream being analyzed in in-line (right in the stream) or on-line (in bypass stream) modes, the sensors should possess satisfactory kinetic response—an ability for fast attainment of equilibrium accumulation in a characteristic time lesser than that of substantial concentration changes in the stream analyzed. The heart of any sensor is immobilized (attached to accessible surface of the sensor) active substance, able to interact selectively with components being determined.

Sensor varieties comprise chemical or biological chips [3-5]—analytical sensors containing set of different active substances in one sensor or set of sensors having different characteristics, each one containing active substance of a certain type. Chemical or biological chip provides information on the mixtures being analyzed not in the numerical form as a response to single measurement, but in the form of some pattern—two-dimensional or three-dimensional image being the compact and exact characteristic ("fingerprint") of the mixture in whole. Although each point of such an image, characterizing presence and concentration of one or another substance, may not be quite correct, the chips allow to ensure essentially full selectivity and unambiguity in analysis due to multiple duplication of such points and to additional information in the form of integral image. The development of chemical and biological chips have began just recently. In literature, notions of electronic (chemical) "nose" or electronic (chemical) "tongue" are also used in respect of chemical chips, in order to underline that selectivity, similar to living organisms, is attained due to a set of sensors having different characteristics [6].

Different types of known chemical sensors [1] include: electrochemical (including potentiometric transducers, such as ion-selective electrodes); electrical sensors on basis of field transistors and other devices, magnetic sensors, thermometric sensors, as well as sensors sensitive to selective component accumulation due to changes in piezoelectrical or acoustical characteristics. Principal drawback of said analytical sensors lies in limited range of the components determined—virtually for each component separate sensor should be designed having certain type of active substance. Besides, it is difficult to create biological sensors on base of approaches specified.

Said drawbacks are eliminated in optical and X ray fluorescent sensors [2], wherein active substance may possess group selectivity to a large number of inorganic, organic or biologically active components. After sorption of these components on immobilized active substance, accessible surface with active substance is treated with exciting radiation by means of UV laser or X ray radiation source. In the first case, fluorescence (luminescence) spectrum is observed in the visible region, and in the second one—X ray fluorescence spectrum. Owing to analytical possibilities of methods specified, allowing to observe separately spectral bands of the components being determined, possibility appears for simultaneous analysis of multicomponent mixtures.

Fluorescent sensors are known in which active substance, interacting with environment components being determined, is applied on (impregnated) or chemically linked to membranes or microgranules of solid porous materials forming sorption layer comprising a large number of monolayers [7]. Principal drawback of said devices lies in the fact that they may not be used as chips allowing to obtain a separate signal from each active surface portion of the sensor.

The drawback specified is eliminated through use of monolayers of microgranules of solid active substances or microvessels with liquid active substances. Fluorescent sensors (biochips) are known [8, 9], wherein active substances, selectively interacting with biologically active macromolecules from the medium being analyzed, are placed in a certain regular manner into channels or pinholes, cut in a special carrier made of glass, quartz, ceramics, plastic or other inert material by lithography or other methods. At present, number of microareas with active substances attainable in such devices doesn't exceed several thousand units. This leads to decrease in sensitivity (detection limits) of the analysis utilizing X-ray fluorescence method.

The most close to the device proposed in technical essence is a fluorescent sensor on basis of multichannel structure, as described in [10]. This sensor is obtained by sintering of a bundle comprising a large number of optical fibers, each one consisting of two coaxial layers formed by two grades of glass or quartz or polymer. One of the end faces of the bundle obtained is treated with chemical substances for etching the internal layers (to a small depth ca. 10 micron) in each fiber, and microspheres of solid active sorbent substance or solid inert substance coated with an active reagent are placed and fixed in the channels formed ("microwells"). Monolayer of microgranules is obtained by way of one microsphere being placed to each channel. Distribution of microspheres in microchannels is achieved by using ultrasonic or other agitation from suspension in volatile liquid, which is then evaporated. Fixation of microspheres in channels is achieved through synthesis of films on surface of the multichannel structure end face from organic substances having different permeability. Another method of fixation involves distribution of microgranules in channels from liquid, in which granule doesn't swell, followed by treatment with another liquid, in which said granule swells and gets fixed. Thus, the device described is a fluorescent sensor on basis of multichannel structures having open microchannels, each one containing sorbent microgranule, in one of the end faces.

Principal drawbacks of said device comprise: complex manufacturing technology, unsatisfactory kinetic characteristics, associated with blocking of substantial part of microgranules surface during their fixation, as well as limited nature of analytical objects, associated with necessity to restrict swelling limits of microgranules in order to preserve integrity of the device. Another drawback of the device specified lies in impossibility to achieve low detection limits for X-ray fluorescent analysis with the use of such sensors. This is due to the fact of external and internal layers of optical fibers being comparable in thickness, so that number of sorbent granules per unit surface of the end face is insignificant, resulting, correspondingly, in equally insignificant density of adsorbed substance being analyzed per unit surface of the end face.

SUMMARY OF THE DISCLOSURE

The invention proposed is aimed at the achievement of technical result consisting in simplification and reducing the costs of fluorescent sensor manufacturing, widening the range of solutions analyzed with one and the same device, improvement in kinetic characteristics of analytical methods utilizing fluorescent sensor, and increase in analysis sensitivity using X-ray fluorescence method.

Fluorescent sensor according to the invention proposed, similar to the most close sensor known from [10], is made on base of multichannel structure with microchannels and comprises sorbent microgranules placed into microchannels on the side of one of the end faces of the multichannel structure.

To achieve this technical result, said multichannel structure in the fluorescent sensor proposed, as distinct from the most close known one, comprises a length of polycapillary tube with through capillaries forming said microchannels. Microchannels are filled with two layers of immiscible substances. One of the layers consists of water or aqueous solution. This layer contains sorbent microgranule. The second layer consists of organic substance.

Thickness of aqueous layer or layer of aqueous solution filling the microchannels, with sorbent microgranule located therein, doesn't exceed 3 millimeters. The reason of this is lies in the fact that further increase in thickness of said layer brings about no improvements in partitioning of said layer and organic substance layer, that is, makes no further contribution to better isolation of sorbent granule from the organic substance, but results instead in the increase of analysis time due to a growth in diffusion time of components being sorbed in aqueous or aqueous solution layer.

Sorbent microgranule in aqueous or aqueous solution layer is arranged advantageously with possibility of its free movement. This ensures possibility of free access of the components being sorbed to the total sorbent microgranules surface, that is, improves kinetic characteristics of the sensor in a wide range of solutions analyzed, in which microgranules may have different swelling properties.

Microgranules placed into different microchannels may belong to one and the same or different sorbents.

The first embodiment is better used for development of sensors allowing for analysis of solutions containing small number of components having independent fluorescent signals.

The second embodiment is better used for development of chips allowing to perform analysis of multicomponent solutions containing large number of components with interfering fluorescent signals.

It is expedient to make polycapillary tube, in particular, of glass or quartz.

This will allow to simplify and reduce costs of manufacture of the source polycapillary tubes, including utilization of technologies developed for these materials.

At that, polycapillary tube for analysis of acid and neutral solutions is better made of glass, as the more cheap material.

For analysis of alkaline solutions, interacting chemically with glass, it is better to make polycapillary tube of quartz.

In particular, it is expedient to make polycapillary tube with thickness of microchannel walls by an order of magnitude smaller than their transverse dimensions.

This relates to the sensors for X-ray fluorescent analysis built up on the additive fluorescence effect from all sorbent granules in the device.

At that, when producing chemical and biological chips for luminescent spectral analysis in the visible region, the polycapillary tube may be made with larger walls thickness in order to avoid merging of signals from each microgranule of corresponding sorbent.

Multichannel structure may be made in the form of straight or curved length of polycapillary tube.

The first embodiment is better used for development of fluorescent sensors, incorporated into analytical units of devices having no special requirements to their compactness associated with a need to analyze solution streams in hard-to-reach points. In this embodiment, the exciting radiation is applied to the end face with microchannels having sorbent microgranules located therein, and source of the exciting radiation is accommodated within said unit.

The second embodiment is better used for development of fluorescent sensors, incorporated into compact analytical units of devices placed in the stream of the solution being analyzed in hard-to-reach points. In this embodiment, the exciting radiation is applied to opposite end face, where there are no sorbent microgranules, and the source of the exciting radiation is accommodated outside of said unit.

However, depending on particular conditions of sensor application, the embodiment of multichannel structure in the form of a straight length of polycapillary tube may turn out to be expedient also in the case of the exciting radiation being supplied from the side of the end face containing no sorbent granules. Conversely, the embodiment of the multichannel structure in the form of a curved length of polycapillary tube may become expedient in the case of the exciting radiation being supplied to the end face with microchannels containing sorbent microgranules.

For multichannel structures made both in the form of straight and curved length of the polycapillary tube, utilization of the sensor is also possible, in which sensor of excited luminescent radiation is located on the side of the end face containing no sorbent microgranules.

Multichannel structure may be also made as a length of polycapillary tube in the form of a tablet, with length smaller than its transverse dimensions.

This embodiment is expedient for more compact analytical devices regardless of the end face of polycapillary tube to which the exciting radiation is supplied.

Organic substance forming one of the above layers filling up microchannels may be either in solid or liquid phase.

The first embodiment is better used for development of fluorescent sensors being arranged in analytical units of the devices in upright position, with aqueous solution layer situated below the layer of organic substance.

The second embodiment is better used for development of fluorescent sensors arranged in analytical units of the devices in an arbitrary position. This embodiment is also preferable in the case when sorbent microgranule may interact not only with substances in aqueous solution, but also with substances in the organic layer.

In all the cases of sensor utilization contemplating accommodation of the source of exciting radiation or sensor of excited luminescent radiation on the side of the end face containing no sorbent granules, the organic substance forming one of the above layers filling up the microchannels (that is, layer adjacent to said end face of the sensor) should be transparent for corresponding radiation (X ray or optical). At that, the length of polycapillary tube should be made with possibility of transporting said radiation.

Thus, the sensor on basis of multichannel structure is proposed. The sensor contains microchannels with sorbent microgranules placed into microchannels on the side of one of the end faces of multichannel structure. The multichannel structure is a length of polycapillary tube with through capillaries forming said microchannels. The latter being filled with two layers of immiscible substances, one of which is formed of water or aqueous solution, and another— of organic substance. Said sorbent microgranules located in microchannels being situated in aqueous or aqueous solution layer.

Several features of embodiment of a sensor in various special cases have been described:

sorbent microgranule may be located in aqueous or aqueous solution layer with possibility of free movement;

microgranules placed into different microchannels may belong to one and the same or different sorbents;

organic substance forming one of the layers filling up microchannels may be either in solid or liquid phase;

said organic substance may be optically transparent or radiolucent, and the length of polycapillary tube may be made with possibility of transporting, correspondingly, optical or X ray radiation;

polycapillary tube may be made, in particular, of glass or quartz;

polycapillary tube may have thickness of its microchannels walls smaller by an order of magnitude than their transverse dimensions;

thickness of said aqueous or aqueous solution layer containing sorbent microgranules doesn't exceed 3 millimeters.

Also three special cases of embodiment of the mentioned multichannel structure have above been described: in the form of a straight or curved length of polycapillary tube and in the form of a tablet.

It is expediently, that the said organic substance is optically transparent or radiolucent, and the length of polycapillary tube may be made with possibility of transporting, correspondingly, optical or X ray radiation. In this case, it is possible any of three said embodiments of the mentioned microchannel structure: in the form of a straight or curved length of polycapillary tube and in the form of a tablet.

Also it is expediently, the allocation of sorbent microgranules in aqueous or aqueous solution layer with possibility of free movement. At such allocation of sorbent microgranules the said organic substance also may by optically transparent or radiolucent, and the length of polycapillary tube may be made with possibility of transporting, correspondingly, optical or X ray radiation. At the specified allocation of sorbent microgranules it is also possible any of three mentioned embodiments of the microchannel structure: in the form of a straight or curved length of polycapillary tube and in the form of a tablet.

Along with the specified allocation of sorbent microgranules in aqueous or aqueous solution layer with possibility of free movement, organic substance forming one of the layers filling up microchannels may be either in solid or liquid phase, and different microchannels can contain granules of one and the same or different sorbents. In these cases multichannel structure may be made in the form of a straight or curved length of polycapillary tube and in the form of a tablet.

In all listed above cases of embodiment of the mentioned multichannel structure (in the form of a straight or curved length of polycapillary tube and in the form of a tablet), it is expediently, to make polycapillary tube with thickness of its microchannels walls smaller by an order of magnitude than their transverse dimensions, and thickness of said aqueous or aqueous solution layer containing sorbent microgranules not exceed 3 millimeters.

Additional advantages and aspects of the disclosure will become readily apparent to those skilled in the art from the following detailed description, wherein embodiments of the present disclosure are shown and described, simply by way of illustration of the best mode contemplated for practicing the present disclosure. As will be described, the disclosure is capable of other and different embodiments, and its several details are susceptible of modification in various obvious respects, all without departing from the spirit of the disclosure. Accordingly, the drawings and description are to be regarded as illustrative in nature, and not as limitative.

BRIEF DESCRIPTION OF THE DRAWINGS

The following detailed description of the embodiments of the present disclosure can best be understood when read in conjunction with the following drawings, in which the features are not necessarily drawn to scale but rather are drawn as to best illustrate the pertinent features, wherein.

DETAILED DISCLOSURE OF THE EMBODIMENTS

Figure 3:
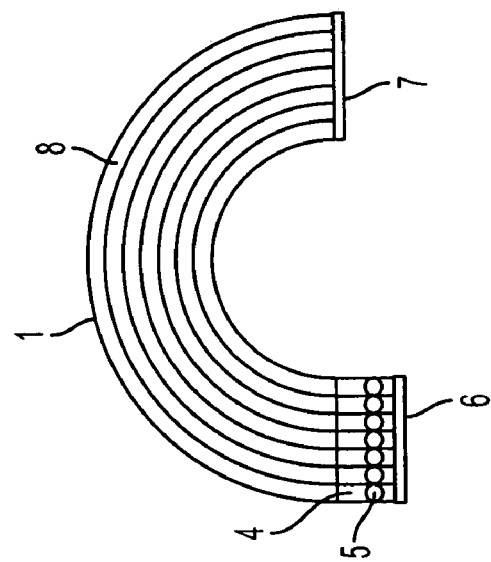
FIG. 3 demonstrates an embodiment of the device in which multichannel structure is made in the form of a tablet.

Fluorescent sensor on basis of multichannel structures according to the invention proposed is constructed as follows. A length 1 of polycapillary tube (FIG. 1), for example, made of glass or quartz, with hundreds of thousand of through capillaries (microchannels) of the same size from units to hundreds micron in transverse section, is hermetically sealed on the side of upper end face with a layer 2 of inert material. Within each microchannel two substance layers are situated. The upper layer 3 is formed of organic substance, and the lower layer 4 is formed of water or aqueous solution. In this layer, sorbent microgranule 5 is located under conditions of free movement, having maximum diameter smaller (for example, by 10-20%) than the internal diameter of microchannel. Lower end face is covered with a layer 6 of inert filtering material having diameter of pores smaller than the diameter of sorbent microgranules.

Multichannel polycapillary structure forming a part of the sensor proposed, in this and other particular embodiments described below may be manufactured, for example, according to methods described in patents [11, 12]. It is possible also to use technology employed in manufacture of polycapillary chromatographic columns, as described in patent [13]. Said technology is preferred if there is a need to ensure small dispersion in cross-sectional dimensions of microchannels.

Figure 2:
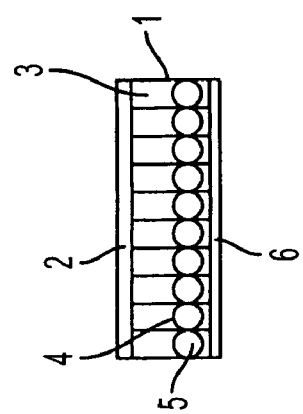
FIG. 2 demonstrates an embodiment of the device comprising multichannel structure in the form of a length of curved polycapillary tube.

Fluorescent sensor on basis of multichannel structures in a variant shown in FIG. 2, comprises also a length 1 of polycapillary tube, hermetically sealed on the upper end face with a layer 2 of inert material. The microchannels formed by capillaries contain an internal layer 3 of organic substance, and a layer 4 of water or aqueous solution with sorbent microgranule 5 freely located in it. Layer 6 of inert filtering material covers the end face on the side of aqueous or aqueous solution layer. The distinctive feature of the device embodiment according to FIG. 2 lies in that it is made in the form of a tablet, manufactured from a length of polycapillary tube, having length smaller than diameter of its end face.

In the embodiment shown in FIG. 3, fluorescent sensor proposed on basis of multichannel structures comprises also a length 1 of polycapillary tube, hermetically sealed or covered on one of the end faces with a layer 7 of inert material. The microchannels formed by capillaries contain an internal layer 8 of organic substance, and a layer 4 of water or aqueous solution with sorbent microgranule 5 freely located in it. Layer 6 of inert filtering material is covering the end face on the side of aqueous or aqueous solution layer.

The distinctive feature of the device according to this embodiment lies in that it is made of a curved length of polycapillary tube. Other features of this device embodiment consist in that the layer 7 of inert material and internal layer 8 of organic substance are radiolucent and/or optically transparent, and that said length of polycapillary tube is made with possibility of transporting, correspondingly, optical or X ray radiation.

In the first case, aggregate microchannels filled up with organic substance serve as a light guide, and in the second one—as a bender, that is, means for transmission and turning of X ray radiation. In this case, total external reflection of radiation from microchannels walls is utilized, and geometry of microchannels, properties of walls material and of organic substance are chosen so as to satisfy the conditions for multiple total external reflection [15, 16].

Figure 1:
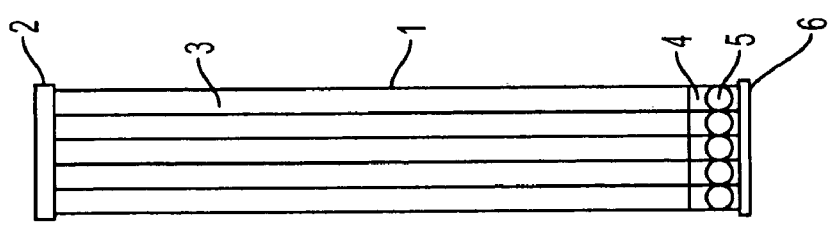
FIG. 1 demonstrates an embodiment of the device comprising multichannel structure in the form of a length of straight polycapillary tube.

Table 1 lists examples of materials used for manufacturing of layer 2 for hermetical sealing or covering of one of the end faces of a straight length of the polycapillary tube (including short lengths, if sensor is made in the form of a tablet) in the cases shown in FIG. 1 and FIG. 2.

TABLE 1

| Nos. | Inert material for layer 2 | Method of end face covering |
|---|---|---|
| 1 | Sealant stable to organic solvents | Sealing with polymerizable sealant |
| 2 | Oil- and petrol-resistant rubber | Use of sealing head with rubber gasket |
| 3 | Silicone | Use of sealing head with silicone gasket |
| 4 | Liquid glass | Sealing with liquid glass followed by hardening |
| 5 | Liquid glass + rubber | Sealing with liquid glass and additional sealing-in using sealing head with rubber gasket |
| 6 | Liquid glass + polyethylene | Sealing with liquid glass and additional sealing-in using sealing head with polyethylene gasket |
| 7 | Liquid glass + polypropylene | Sealing with liquid glass and additional sealing-in using sealing head with polypropylene gasket |
| 8 | Liquid glass + teflon | Sealing with liquid glass and additional sealing-in using sealing head with teflon gasket |
| 9 | Paraffin + rubber (or silicone) | Sealing with liquid paraffin with subsequent packing |
| 10 | Paraffin + polyethylene (or polypropylene or teflon) | Sealing with liquid paraffin with subsequent packing |

Table 2 lists examples of inert radiolucent (<<RL>>) and/or transparent to ultraviolet on (<<UVT>>) materials for manufacturing of layer 7 for hermetical sealing or covering of the end faces of a length of curved polycapillary tube in the case shown in FIG. 3.

TABLE 2

| Nos. | Inert material for layer 7 | Method of the end face covering |
|---|---|---|
| 1 | RL, UVT Thermoplastic hot-melt adhesives on basis of polyethylene | Sealing of the end face with subsequent setting |
| 2 | RL, UVT Polyethylene film + thermoplastic adhesives (solutions on basis of polystyrene) | Sealing with adhesive applcation on the film (engaging the upper part of outer wall of polycapillary tube) followed by curing |
| 3 | RL, UVT Cellophane film + thermoplastic adhesives (solutions on basis of polystyrene) | Sealing with adhesive applcation on the film (engaging the upper part of outer wall of polycapillary tube) followed by curing |
| 4 | RL Thermoplastic hot-melt adhesives on basis of ethylene-vinylacetate copolymer | Sealing of the end face followed by setting |

Table 3 lists examples of organic substances forming internal layer 3 of sensors made of a straight length of polycapillary tube, including those in the form of a tablet, shown in FIG. 1 and FIG. 2, or internal layer 8 of sensor made of a curved length of polycapillary tube shown in FIG. 3.

TABLE 3

| Nos. | Substance | Physical state: Liquid—<<L>>; Solid—<<S>>; Radiolucent—<<RL>>; Transparent for ultraviolet radiation—<<UVT>> |
|---|---|---|
| 1 | Hexane | L, RL, UVT |
| 2 | Heptane | L, RL, UVT |
| 3 | Octane | L, RL, UVT |
| 4 | Gasoline | L, RL, UVT |
| 5 | White spirit | L, RL, UVT |
| 6 | Benzene | L, RL |
| 7 | Toluene | L, RL |
| 8 | Paraffin | S, RL |
| 9 | Polyacrylamide | S, RL |
| 10 | Polyacrylonitrile | S, RL |
| 11 | Polystyrene | S, RL |

Table 4 lists examples of sorbents constituting the microgranules 5 placed into layer 4 of water or aqueous solution.

TABLE 4

| Nos. | Sorbent material | Functional group |
|---|---|---|
| 1 | Strong-acid gel and macroporous cationites: KU-2, KU-23, Dowex-50, Dowex-HCR, Dowex-MSC, Dowex-Marathon C, Purolite C100, Amberlite GOL, Amberjet, Lewatit S, Lewatit SP | —$SO_3^-$ |
| 2 | Weak-acid gel and macroporous cationites: KB-2, KB-4, Dowex MAC, Purolite C105, Amberlite IRC, Lewatit SNP | —$COO^-$ |
| 3 | Strong-base gel and macroporous anionites: AV-17, AV-171, Dowex-2, Dowex-MSA, Purolite A400, Amberlite IRA, Lewatit M | —$N(R_4)^+$ |
| 4 | Weak-base gel and macroporous anionites: AN-31, AN-221, AN-511, Dowex MWA, Purolite A100, Lewatit MP | —$NH_k(R_{4-k})^+$ where k = 1, 2, 3 |
| 5 | Gel and macroporous polyampholytes: ANKB-50, Tulsion | —$SO_3^-$ + —$NH_k(R_{4-k})^+$ or —$COO^-$ + —$NH_2$ |
| 6 | Selective sorbents for analytical chemistry of the <<Polysorb>> type | —C(R)=N—OH; —CO—N(R)=OH; —C(OH)—C(R)=N—OH; —N(R)—C(S)—S(Na); —N—(NO)—$ONH_4$; —$CH_2$(R)—N($CH_2COONa)_2$, where R denotes organic radical, and other amidooxime, hydrazine, dithiozone, diacetate groups |
| 7 | Impregnated sorbents | Impregnation with: liquid ionites: complexing organic agents, extractants. |
| 8 | Neutral polymeric matrices with subsequent chemical cross-linking of functional group | Crosslinking: oligomers and monomers with ion-exchange groups: complexing organic agents and extractants |
| 9 | Inorganic sorbents containing no components to be determined | Aluminosilicate, oxide, phosphate |
| 10 | Sorbent supports for affinity chromatography of biopolymers | CM-celulose, DEAE-celulose, Agarose, Sephadex, Hydroxyalkylmethacrylate, Polyvinylacetate |

Table 5 lists examples of inert filtering materials for layer 6 covering the end face on the side of aqueous or aqueous solution layer.

TABLE 5

| Nos. | Material (a film 1-20 micron thick) diameter of openings - 1-10 micron | Network—<<N>>, Membrane—<<M>> Radiolucent—<<RL>> Transparent to ultraviolet radiation—<<UVT>> Transparent in the visible region—<<VT>> |
|---|---|---|
| 1 | Caprone | N, RL, UVT |
| 2 | Nylon | N, RL, UVT |
| 3 | Glass fibre cloth | N |
| 4 | Polyacetate | M, RL, UVT |
| 5 | Polyethylene | M, RL, UVT, VT |
| 6 | Teflon | M, RL, UVT, VT |
| 7 | Polypropylene | M, RL, UVT, VT |
| 8 | Cellophane | M, RL, UVT, VT |

In manufacture of the fluorescent sensor proposed on basis of multichannel polycapillary structure, capillary rise effect may be utilized for liquids possessing wetting ability. Manufacturing of device with a layer of liquid organic substance in microchannels comprises following stages.

A. Sorbent material is preliminarily ground in a ball mill, after which the powder obtained is separated into narrow fractions by column sedimentation in 0.1M sodium chloride solution. Fractions required for a given type of sensor are collected, for example, for polycapillary tubes with isolated channels of 20 micron size, fractions are collected with limiting grain size of 15-17 micron.

Figure 4:
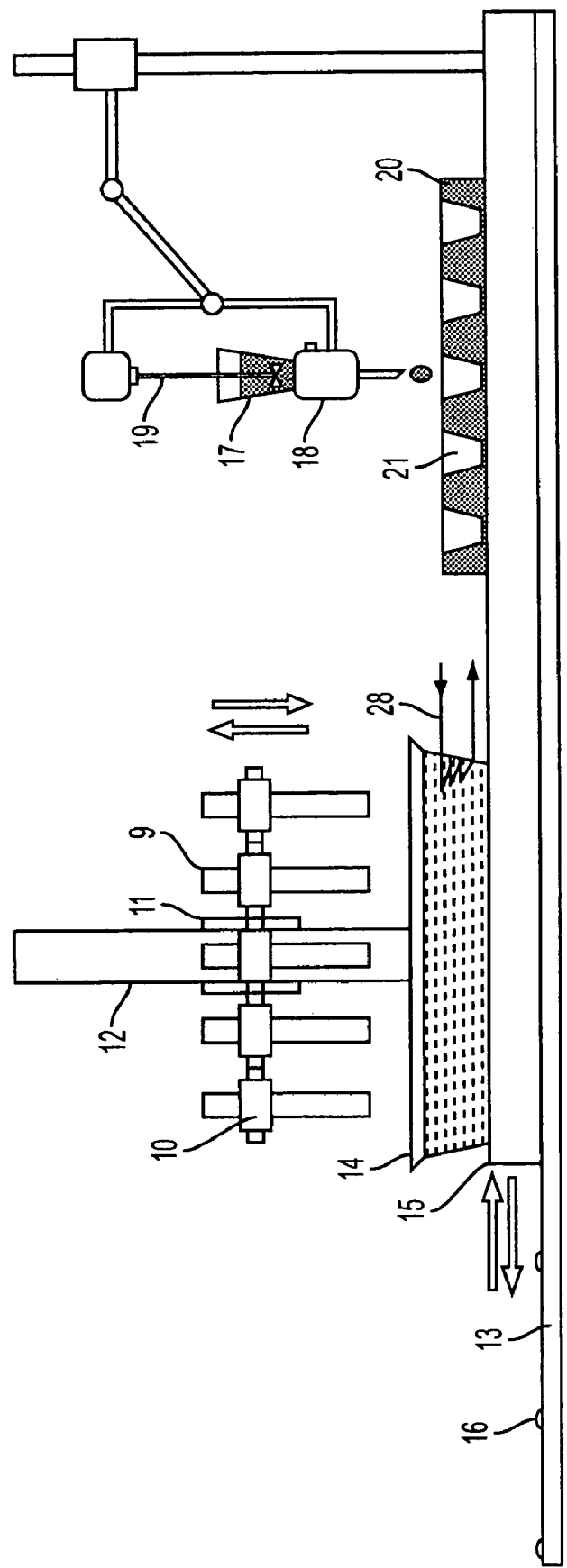
FIG. 4 shows schematically an example of a sensors manufacturing plant.

B. Workpieces of polycapillary columns 9 (lengths of straight polycapillary tubes) are fastened in clamps 10 of an adjustable height holder 11 sliding over the stand 12 mounted on stationary frame 13 (FIG. 4). By means of holder 11 polycapillary columns 9 are immersed to the half of their length into vessel 14 containing organic liquid, placed on movable stage 15, mounted in its turn on a frame 13. Stage 15 may travel on guide rollers 16 both in free and in controlled indexing mode.

Organic liquid should possess following properties:

it should be wetting the material of microchannels walls of polycapillary columns, but to a lesser extent than water;

liquid shouldn't be miscible with aqueous phase;

liquid should be lighter than water.

For example, hexane may be selected as such liquid. All columns are completely filled with hexane over the course of 5 min. due to capillary forces.

C. Mass of a number of sorbent particles corresponding to the number of channels is calculated and weighed out beforehand. For example, in order to place one sorbent granule into each 20-micron microchannel in polycapillary column having 400,000 microchannels, it is necessary to have 1 mg of sorbent fraction having particle size 15-18 micron and density 1.1 g/cm3; to make simultaneously 100 sensors, it is necessary to have 100 mg of sorbent.

D. Working suspension is prepared. To the weighed amount of sorbent placed into glass microvessel 17 equipped with automatic drop feeder 18 and mixing microdevice 19, 100 drops (by the number of sensors manufactured) (5×10-2 cm3 each) of concentrated sodium chloride solution having density equal to density of sorbent, are introduced with another liquid metering unit (dropper) and the mixture is agitated to obtain stable suspension.

E. Use is made of hydrophobic plate 20 (for example, made of polyethylene) positioned on movable stage 15 with wells 21 cut out in the form of truncated cone, their arrangement and spacings corresponding to positions of clamps 10 of the holder 11 and distances between them. By adjusting advance of centers of conical wells 21 to the suspension microfeeder 18 and performing coordinated dosing of drops, one drop of suspension is placed into each one of 100 wells.

F. Level of holder 11 is lifted for a short time, glass vessel 14 containing hexane is drawn aside, hydrophobic plate 20 with suspension drops in conical wells 21, mounted on movable stage 15, is placed under the holder and the stage is fixed in a strictly calculated position. The holder 11 is pulled down in such a way that the lower end of each polycapillary column 9 would come into contact with corresponding drop of suspension. In the course of ca. 30 s suspension is drawn (total drop without remainder) into the column due to capillary forces.

Figure 5:
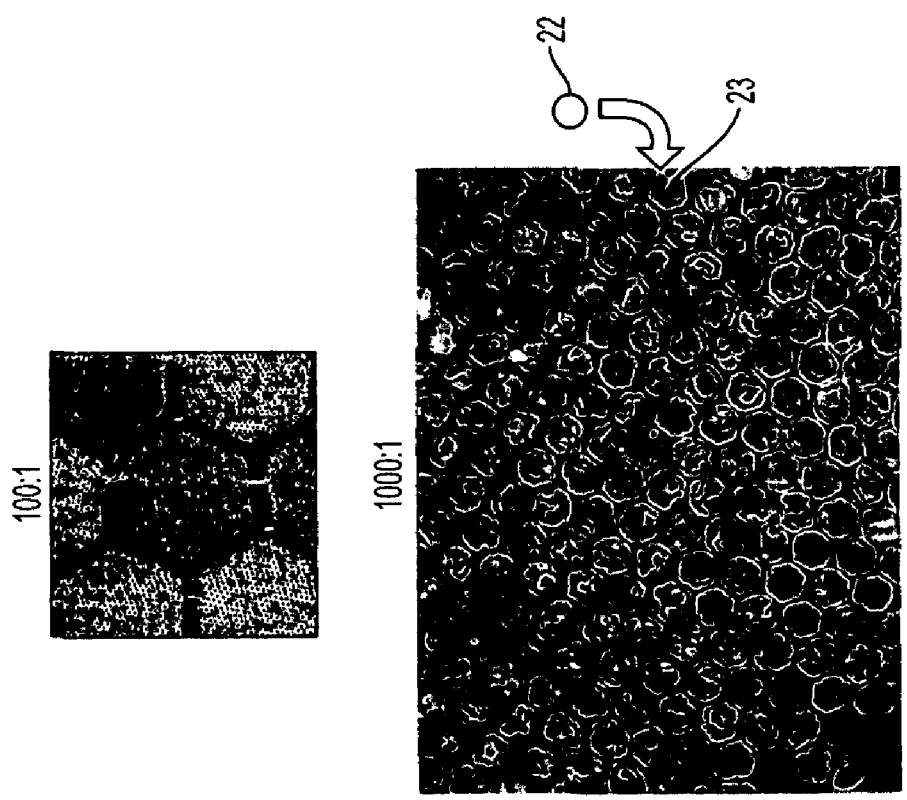
FIG. 5 shows photomicrographs of open lower end face of the polycapillary tube.

Photomicrographs of the lower end face of column taken at different magnification scales, shown in FIG. 5, allow to demonstrate scheme of sorbent grain 22 inclusion into isolated microchannel 23 of the multichannel structure.

G. The upper end faces of polycapillary columns are sealed by one of methods described in Tables 1 or 2.

Figure 6:
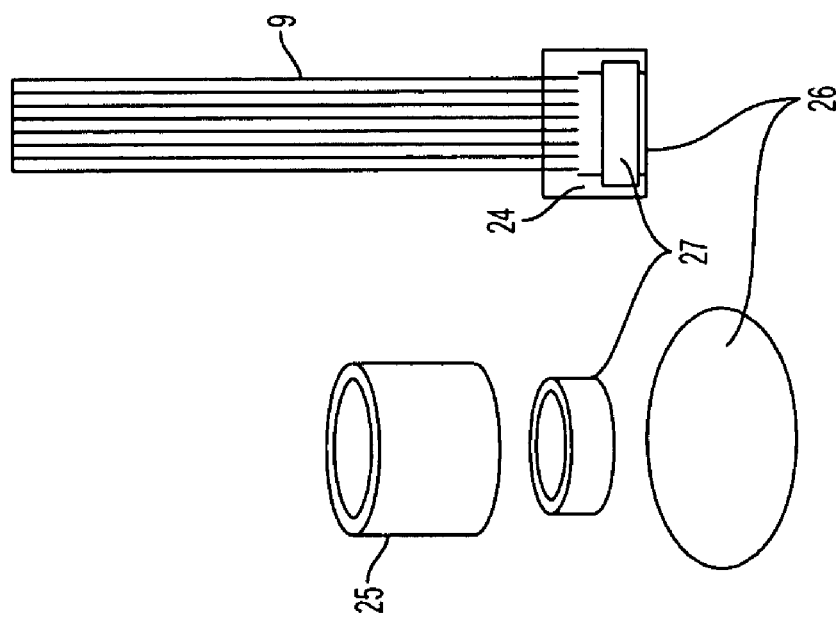
FIG. 6 demonstrates an example of structure of a special cap having microporous bottom forming the lower part of the sensor.

H. The lower part of each ready sensor is covered with special cap 24 (FIG. 6) having side walls made of a length 25 of silicone tube, tightly adjoining the outer wall of polycapillary column 9. Bottom of the cap 24 is formed by a net or microporous membrane 26 stretched over plastic cylindrical ring 27 and glued, as shown in FIG. 6, with one side to the outer surface of said cylindrical ring 27, and with the other side—to internal surface of a length 25 of silicone tube. Examples of corresponding nets or membranes are listed in Table 5. In particular, 10-micron nylon screen filter is used (standard Millipore product). This variant is used in the case when sorbent microgranules are larger than 10 micron in size. In all the other embodiments, a membrane is used instead of screen microfilter, for example, polyacetate membrane having micropores of 5 micron or less (standard Millipore product), selected in accordance with dimensions of sorbent microgranules. Before mounting the cap on the lower part of sensor, the internal surface of silicone tube, directly adjoining the external surface of polycapillary tube, is coated with a thin layer of polymerizing water-repellent sealant (adhesive).

Manufacturing of device with solid organic layer, for example, paraffin, comprises the above stages A, C, D, E, and H, and differs in embodiment of stages B and F (see below, correspondingly, B1 and F1), as well as in the stage G being omitted.

B1. Workpieces of polycapillary columns are immersed using adjustable height holder 11 (FIG. 4) into vessel 14, placed on movable stage 15 and containing molten paraffin instead of hexane, to a level by 1-2 mm below the upper end face of columns. Paraffin is melted and maintained in the molten state due to heat-exchange tube 28 being inserted into the vessel, with hot water (or silicone oil) supplied from an external thermostat.

In the course of 30 min. all columns are completely filled up with liquid paraffin due to capillary forces. After that, polycapillary columns are raised to such a level that only lower part of polycapillary columns with no more than 3 cm height would remain in liquid. The system is maintained in this position for 10 min., permitting the paraffin in nonimmersed part of the columns to cool down and solidify.

F1. Level of holder 11 is lifted for a short time, glass vessel 14 containing liquid paraffin is drawn aside by moving the stage 15, and hydrophobic plate 20 with suspension drops is placed under the holder and fixed in a strictly calculated position. The holder 11 is pulled down in such a way that lower end of each polycapillary column would come into contact with corresponding drop of suspension. Due to reduction of paraffin volume on cooling and solidification (by approximately 5%) in the lower part of the columns, the suspension drop is drawn completely into the column in the course of ca. 300 s (without remainder).

Manufacturing of the device comprising different sorbents (fluorescent chip) with liquid or solid organic layer is similar to the above embodiments and differs only in realization of stages C and D (see below, correspondingly, C1 and D1)

C1. Mass of a number of sorbent particles corresponding to the number of channels is calculated and weighed out beforehand. For example, if using 10 different sorbents and selecting polycapillary tube having 400,000 of 20-micron channels, it is necessary to have 100 µg of each sorbent (see Table 4) with particle size 15-18 micron and density 1.1 g/cm3. To make 100 sensors simultaneously, it is necessary to have 10 mg of each sorbent.

D1. Working suspension is prepared. 100 drops (5410-2 cm3 each) of concentrated sodium chloride solution with density equal to the density of sorbent are introduced to the weighed amount of sorbent mixture, placed into glass microvessel 17 equipped with automatic drop feeder 18 and mixing microdevice 19, with the help of another similar dosing unit, and the mixture is agitated to obtain stable suspension.

The process of sensors manufacturing comprises stage of their selective testing to determine content of working sorbent and rate of sensors functioning.

The sensor under test is kept for 10 min. in a beaker with 0.1N hydrochloride acid solution (while agitating the solution) and then washed three times in distilled water. pH meter is used to ascertain that pH of the distilled water remains unchanged in the presence of sensor.

Figure 7:
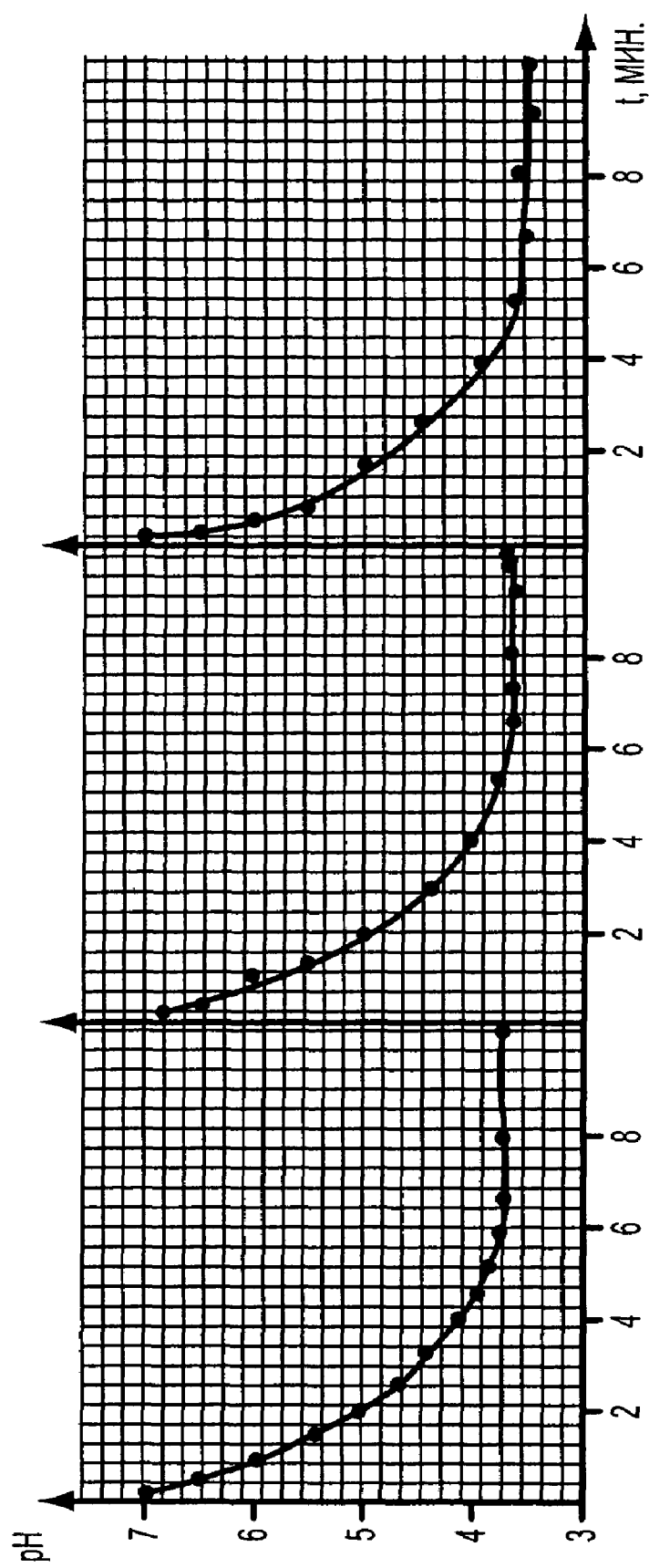
FIG. 7 shows potentiometric curves for testing the operability of sensors.

After that, sensor is put into a beaker with 20 ml of 0.01N NaCl solution placed under the pH-meter, and changes in solution pH with time are followed under continual stirring. Such a change, namely, acidification of the solution, takes place due to ionic exchange Na+–H+. Testing is repeated at least twice in order to ascertain reproducibility of the results. FIG. 7 demonstrates that the results are virtually completely reproduced. The time to attainment of plateau region on the curves presented (ca. 7 min.) corresponds to equilibration time, that is, is indicative of kinetic characteristics of the sensor, while drop in pH value shows exchange capacity. It is seen from curves in FIG. 7, that this drop corresponds to a change from pH=6.8-7.0 to pH=3.60-3.75. In terms of exchange capacity, it corresponds to 4.3-4.4 µg-eq, and taking into account tabulated capacity of KU-2 cationite, equal to 4-4.5 mg-eq/g, it may be seen that 1 mg of cationite is "working".

The sensors obtained may be used for analytical control of different solutions. Examples of control units design are shown in FIG. 8-11. In these Figures: 29—flow-through cell; 30—sensor; 31—vessel with solution being tested; 32—pump; 33—ultrasonic sorption activator; 34—X ray excitation source of X-ray fluorescent spectral analyzer; 35—X-ray fluorescent sensor; 36—signals converter; 37—computer; 38—source of UV radiation (UV laser); 39—waveguide for UV excitation; 40—luminescence sensor; 41—luminescent spectral analyzer; 42—sensor with radiolucent layer of organic substance, made of curved polycapillary tube; 43—sensor with a layer of optically transparent organic substance, made of a length of polycapillary tube in the form of a tablet; 44—waveguide for luminescent radiation in the visible region.

Operation of sensors incorporated into analytical units specified is described below.

When utilizing X-ray fluorescence method, flow-through solutions consisting of flushing waste waters of electroplating manufacture (copper and zinc plating) after production stage of their purification by ionic exchange have been selected as control object for analysis. Content of nonferrous and heavy metal ions in such purified solutions doesn't exceed few tens of µg/l. Therefore, these purified solutions are allowed to be discharged to natural water reservoirs of fishing industry use.

At the same time, detection limits of X-ray fluorescence method in direct solution analysis are at the level of several tens of mg/l.

Figure 8:
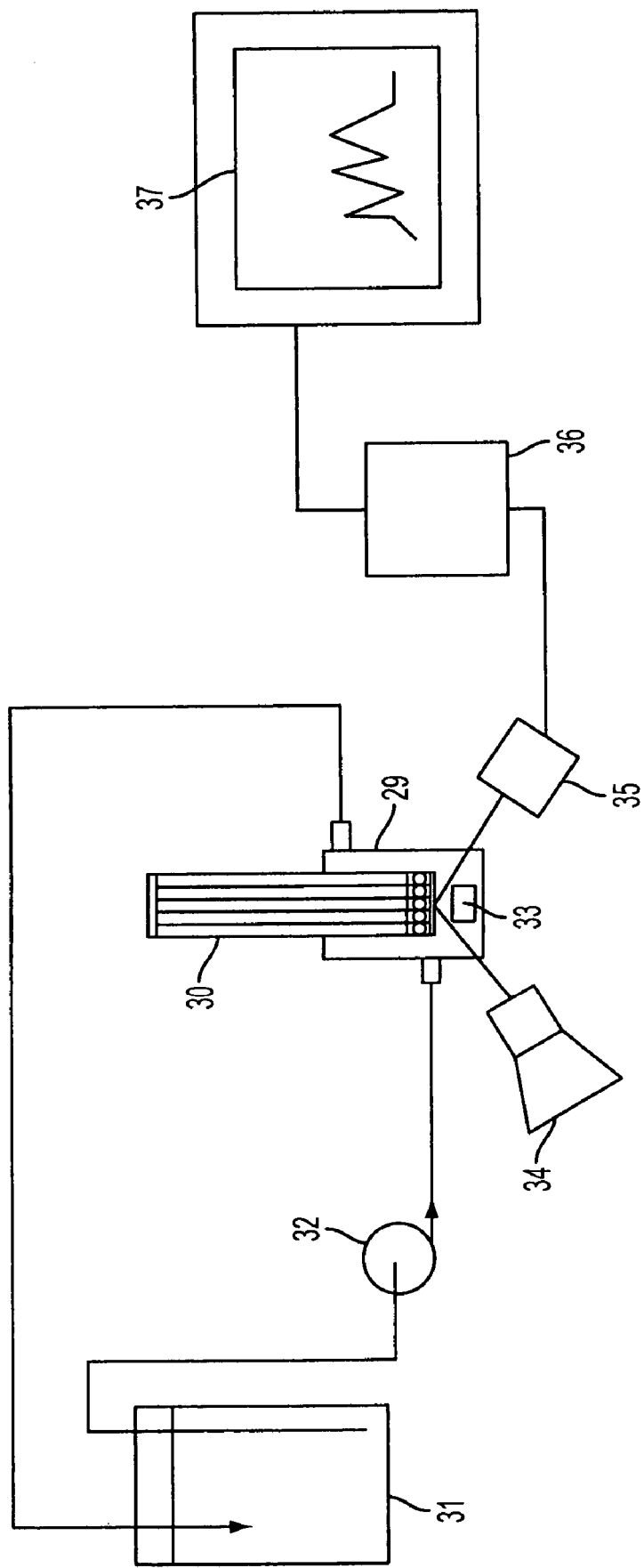
FIG. 8 shows utilization of sensor proposed incorporated into analytical device for X-ray fluorescent analysis of solutions.

The solution tested from vessel 31 had been passed with pump 32 in the course of 30-120 min. through cell 29 with sensor 30 immersed (FIG. 8). After said treatment, corresponding spectra have been registered with X ray fluorescent device "Focus" [14]. To desorb accumulated elements and restore sensor for use in subsequent analyses, the sensor was immersed with its lower end (containing sorbent) into 0.1N hydrochloric acid solution and held in it for 15 min.

Figure 12:
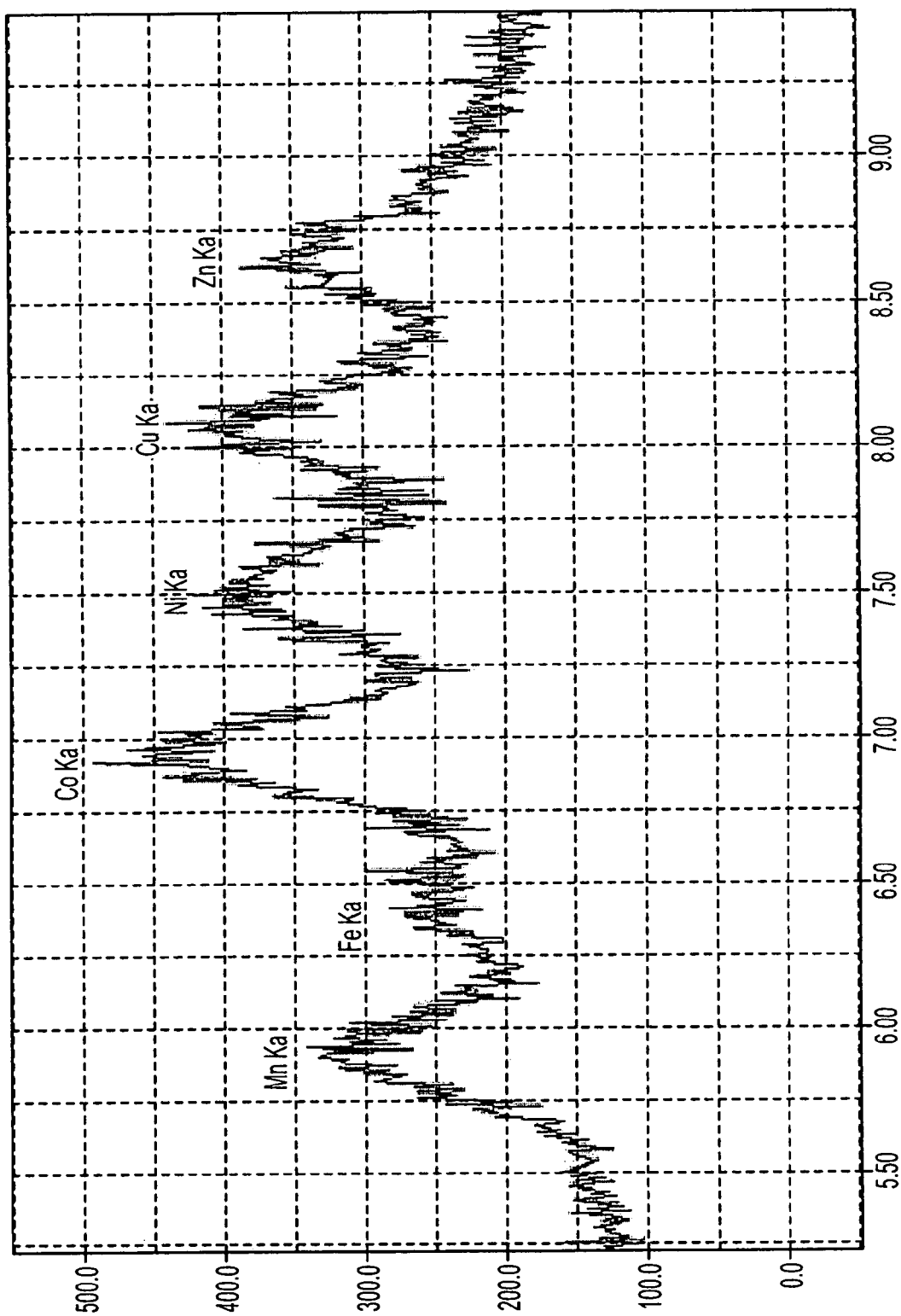
FIGS. 12-14 show X ray fluorescence spectra registered during analysis of different solutions utilizing the sensor proposed on basis of multichannel structure.
Figure 13:
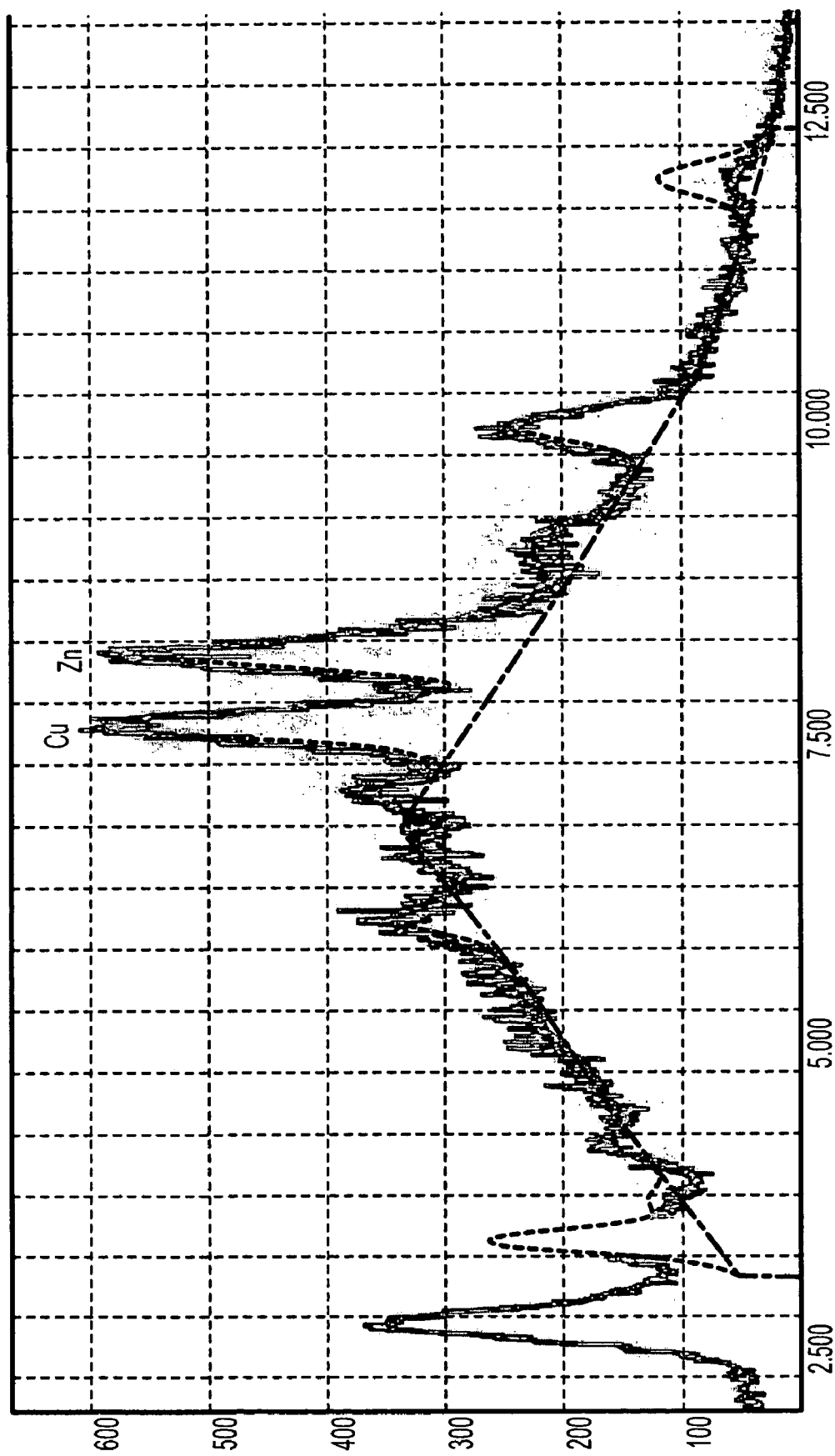
Figure 14:
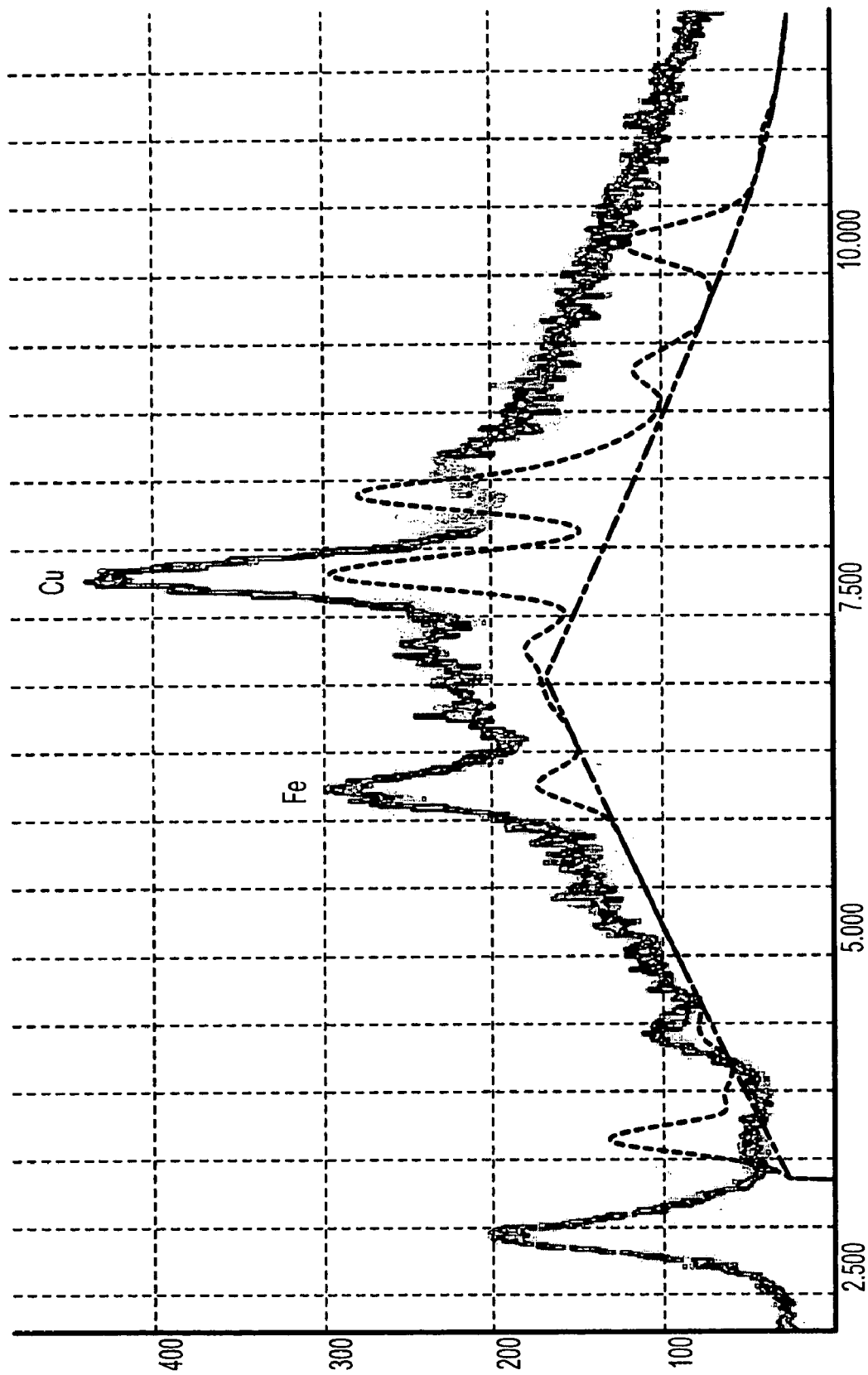

FIGS. 12-14 demonstrate X ray fluorescence spectra registered with apparatus shown schematically in FIG. 8 utilizing sensors made of straight lengths of polycapillary tubes of 10 cm height employing as a layer of organic substance paraffin (FIG. 12 and FIG. 14) and hexane (FIG. 13) layers for following variants of sensor make:

in FIG. 12 sensors are made of lead glass, comprise 400,000 microchannels having diameter of isolated microchannel 20 micron and walls thickness between them 2 micron, each one containing microgranule of 16 micron in size made of strong-acid cationite KU-2 on basis of styrene and divinylbenzene with sulphonic functional groups;

in FIG. 13 sensors are made of lead glass, comprise 1,000,000 microchannels having diameter of isolated microchannel 10 micron and walls thickness between them 1 micron, each channel containing microgranule of 8 micron in size made of strong-acid cationite KU-2 on basis of styrene and divinylbenzene having suphonic functional groups;

in FIG. 14, sensors are made of leadless glass, comprise 1,000,000 microchannels having diameter of isolated microchannel 10 micron, each channel containing microgranule of 8 micron in size made of weak-acid cationite KB-4 on basis of polymethylmethacrylate with carboxylic functional groups.

Concentrations of components being determined in washing water, found at different time periods utilizing fluorescent sensors, amount to: in FIG. 12: Fe—30 µg/l; Cu—90 µg/l; Ni—60 µg/l; Mn—200 µg/l; Co—320 µg/l, Zn—120 µg/l, total time of accumulation and analysis—30 min.; in FIG. 13, 14: Cu—50 µg/l; Fe—30 µg/l; Zn—50 µg/l, total time of accumulation and analysis—120 min.

As it is seen from spectra presented, use of fluorescent sensors proposed according to the invention allows to determine with confidence components content, 1,000 times smaller than that attainable for direct analytical control without sensors, thus bringing the X-ray fluorescence method to the level of methods for monitoring natural and waste waters.

Figure 9:
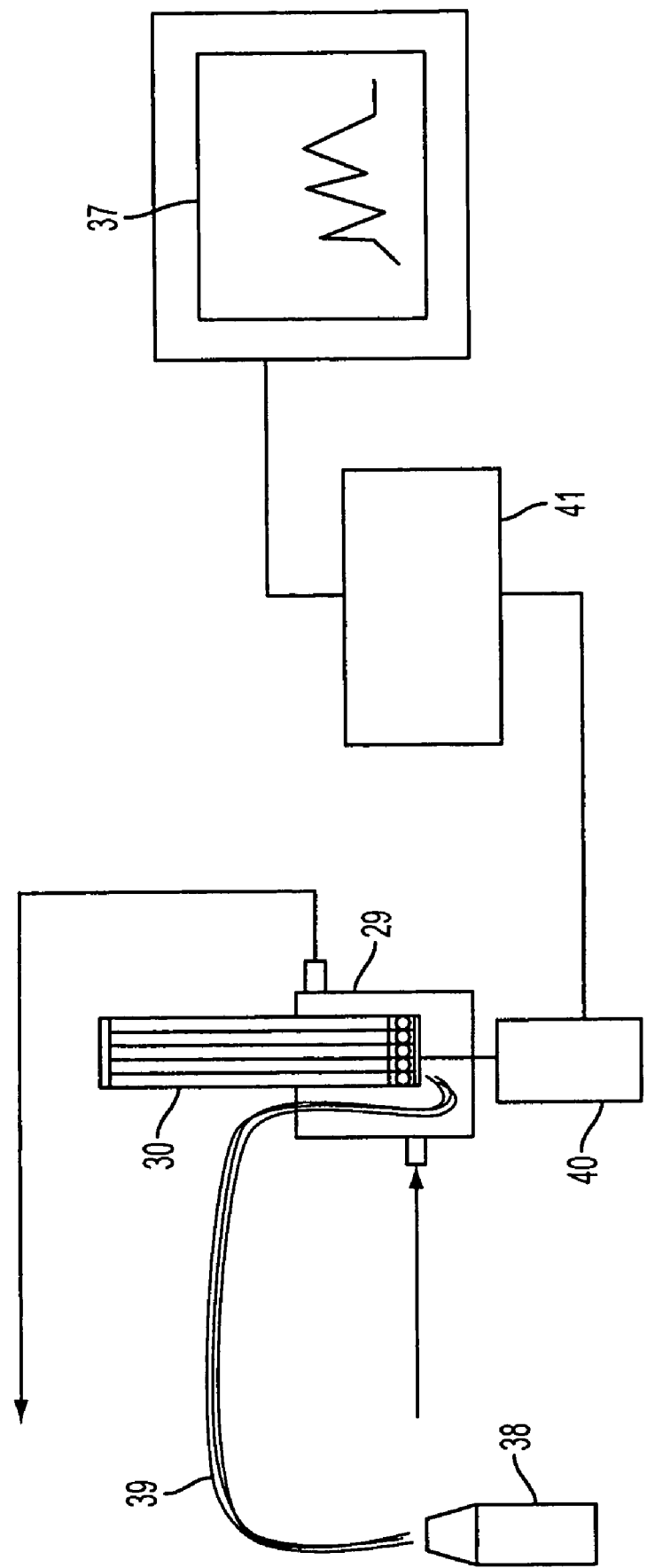
FIG. 9 shows utilization of sensor proposed incorporated into analytical device for luminescent analysis of solutions in the visible region.

Fluorescent sensors intended for use in the region of visible luminescence, excited by ultraviolet radiation supplied to the end face containing sorbent microgranules, are utilized as a part of analytical device shown in FIG. 9. Analysis of continuous flow solutions containing organic luminophors or biologically active molecules with crosslinked luminescently active probes is performed by technique similar to that described above for X ray fluorescence, except that the most appropriate source of the exciting radiation is a UV-laser, and registering instrument—luminescent spectral analyzer. The detection limits of the components (organic or biologically active substances) being determined with use of said sensors decrease in proportion to accumulation coefficient of corresponding sorbents, listed in line 10 of Table 4, namely, by a factor of $10^2$-$10^4$.

Figure 10:
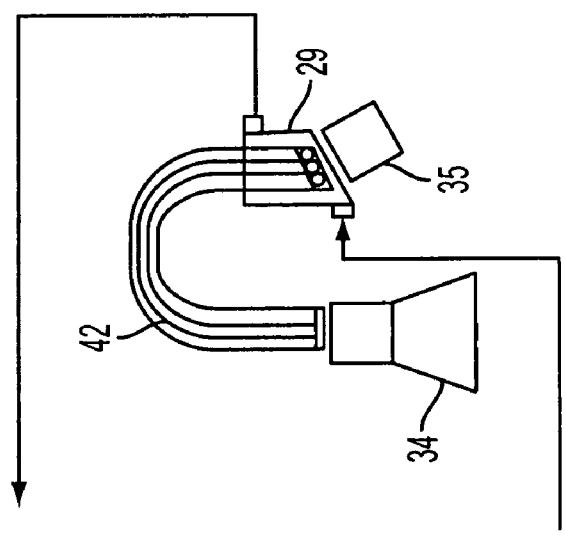
FIG. 10 shows utilization of sensor proposed with optically transparent organic substance forming one of the layers filling up microchannels, incorporated into analytical device for X-ray fluorescent analysis of solutions.

Fluorescent sensors made of a curved length of polycapillary tube having radiolucent or UV-transparent upper layer and internal radiolucent or UV-transparent layer of organic substance, are used in analytical device shown in FIG. 10.

Figure 11:
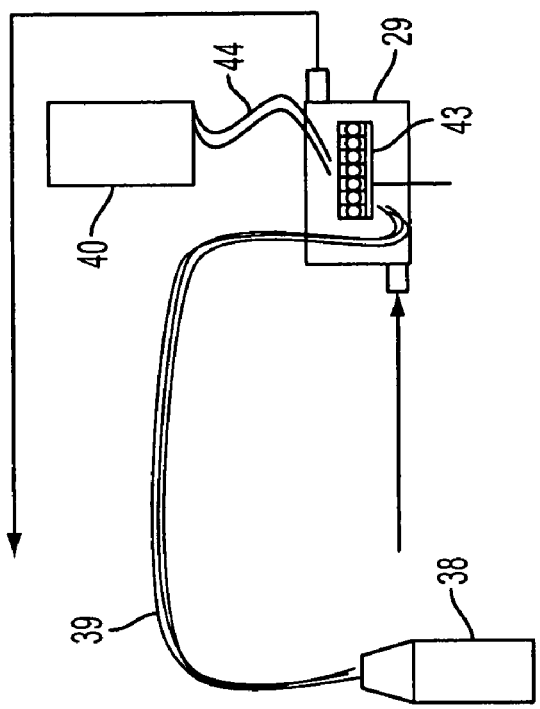
FIG. 11 shows utilization of sensor proposed with optically transparent organic substance forming one of the layers filling up microchannels, incorporated into analytical device for luminescent analysis of solutions in the visible region.

Fluorescent sensors made of a length of polycapillary tube in the form of a tablet with UV-transparent upper layer and internal UV-transparent layer of organic substance are used in analytical device shown in FIG. 11.

Analysis of continuous flow solutions containing components being determined, in particular, non-ferrous and heavy metals, as well as luminescently active organic and biological substances, is performed by techniques similar to those described above, except that, as shown in Figures specified, the exciting X ray radiation from source 34 is supplied to the side of the end face not submerged into solution analyzed (FIG. 10), or except that the luminescent radiation in the visible region is transported to sensor 40 with the help of a waveguide 44 (FIG. 11).

The detection limit of the components being determined using said sensors decreases in proportion to accumulation coefficient of corresponding sorbents, described in Table 4. In particular, the detection limit of metals decreases 103-105 times, and that of organic and biologically active substances—102-104 times.

Fluorescent sensors having different sorbents located in microchannels, namely, fluorescent chips, are used in analytical devices similar in design to those shown in FIG. 8-11. However, sensor 35 in FIG. 8 and FIG. 10 is a raster (two-coordinate) X ray sensor, while sensor 40 in FIG. 9 and FIG. 11 is a two-coordinate sensor in the visible region (electronic photocamera). When using X-ray fluorescence method, the analytical result for each characteristic X ray fluorescence band of chemical element determined is brought out in the form of three-dimensional diagram: signal intensity vs. sorbent microgranules coordinates (position) in the end face of a sensor (chip).

When utilizing luminescence in the visible region, the analytical result for each luminescence wavelength of organic or biological compound being determined, containing luminophor, or each de-excitation wavelength of luminophor contained in sorbents, characteristically shifted under the influence of inorganic or organic component determined (adsorbed), is brought out in the form of three-dimensional diagram: light signal intensity versus sorbent microgranules coordinates in the end face of a sensor (chip).

Processing of test results in these cases is performed by a procedure similar to that described in [10].

The embodiments described hereinabove are further intended to explain best modes known of practicing the invention and to enable others skilled in the art to utilize the invention in such, or other, embodiments and with the various modifications required by the particular applications or uses of the invention.

Accordingly, the description is not intended to limit the invention to the form disclosed herein. Also, it is intended that the appended claims be construed to include alternative embodiments.

SOURCES OF INFORMATION

1. G. K. Budnikov, What is chemical sensors//Soros Educational Journal, 1998, No. 3, P. 72-76 (in Russian).

2. Fluorescent Chemosensors for Ion and Molecule Recognition, ACS Symp. Ser./ed. A. W. Czarnik//AChS Publ., Washington, D.C. 1992, 225 p.

3. Reviews: The Chipping Forecast//Nature Genetics, 1999, V. 21, P. 1-60.

4. Gilbert W., DNA sequencing and gene structure/Science, 1981, V. 214, P. 1305-1312.

5. V. Barskij, A. Kolchinskij, Yu. Lysov, A. Mirzabekov, Biological microchips containing nucleic acids, proteins and other compounds immobilized in hydrogel: properties and applications in genomics//Molekulyarnaya Biologiya (Molecular Biology), 2002, T. 36, P. 563-584 (in Russian).

6. S. Ampuero, J. O. Bosset, The electronic nose applied to dairy products: a review//Sensors and Actuators B: Chemical, 2003, V. 94, P. 1-12.

7. Seitz W. R., Fiber optic sensors//Anal. Chem., 1984, V. 86, No. 1, P. 16-25.

8. Patent of Russian Federation No. 2157385, publ. Oct. 10, 2000.

9. P. Zhang, T. Beck, W. Tan, Design a molecular beacon with two dye molecules, Angewandte Chemie International Edition, 2001, V. 40, P. 402-405.

10. U.S. Pat. No. 6,023,540, publ. Feb. 8, 2000.

11. Patent of Russian Federation No. 2096353, publ. Nov. 20, 1997.

12. Patent of Germany No. 4411330, publ. Aug. 14, 2003.

13. Patent of Russian Federation for utility model No. 31859, publ. Aug. 27, 2003.

14. A. S. Scherbakov, S. M. Cheremisin, V. V. Danichev, V. S. Ozerov, Focus-1 X-ray fluorescent spectrometer, Proceed. SPIE, 2000, V. 4155, P. 131-137.

15. V. A. Arkad'ev, A. P. Kolomijtsev, M. A. Kumakhov, I. Yu. Ponomarev, I. A. Khodeev, Yu. P. Chertov, I. M. Shakhparonov. Wide-band X-ray optics with a large angular aperture. Uspekhi Fizicheskikh Nauk (Advances in Physical Sciences), March 1989 r., V. 157, Issue 3, p. 529-537 (in Russian).

16. U.S. Pat. No. 5,192,869, publ. Mar. 09, 1993.

What is claimed is:

1. Fluorescent sensor on the basis of multichannel structure, comprising:
   microchannels having sorbent microgranules placed into the microchannels at one of end faces of the multichannel structure,
   the multichannel structure being a piece of a polycapillary tube with through capillaries forming the microchannels,
   the microchannels being filled with two layers of immiscible substances, one of which is formed of water or aqueous solution, and another is formed of organic substance, said sorbent microgranules located in the microchannels being situated in aqueous or aqueous solution layer.

2. Sensor according to claim 1, characterized in that said aqueous or aqueous solution layer is configured to provide free movement of said sorbent microgranules.

3. Sensor according to claim 2, characterized in that said organic substance is in a liquid phase and the microchannels contain granules of different sorbents.

4. Sensor according to claim 2, characterized in that said organic substance is in a liquid phase and the microchannels contain granules of the same sorbent.

5. Sensor according to claim 2, characterized in that said organic substance is in a solid phase and the microchannels contain granules of the same sorbent.

6. Sensor according to claim 2, characterized in that said organic substance is in a solid phase and the microchannels contain granules of different sorbents.

7. Sensor according to claim 3, characterized in that said organic substance is optically transparent or radiolucent, and said polycapillary tube is configured for transporting optical or X ray radiation, respectively.

8. Sensor according to claim 7, characterized in that said multichannel structure is made in the form of a straight length of polycapillary tube.

9. Sensor according to claim 7, characterized in that said multichannel structure is made in the form of a curved length of polycapillary tube.

10. Sensor according to claim 7, characterized in that said multichannel structure is made as a length of polycapillary tube in the form of a tablet having length less than its transverse dimensions.

11. Sensor according to claim 4, characterized in that said organic substance forming one of the layers filling up microchannels is optically transparent or radiolucent, and said length of polycapillary tube is made with possibility of transporting, correspondingly, optical or X ray radiation.

12. Sensor according to claim 11, characterized in that said multichannel structure is made in the form of a straight length of polycapillary tube.

13. Sensor according to claim 11, characterized in that said multichannel structure is made in the form of a curved length of polycapillary tube.

14. Sensor according to claim 11, characterized in that said multichannel structure is made as a length of polycapillary tube in the form of a tablet having length less than its transverse dimensions.

15. Sensor according to claim 5, characterized in that said organic substance forming one of the layers filling up microchannels is optically transparent or radiolucent, and said length of polycapillary tube is made with possibility of transporting, correspondingly, optical or X ray radiation.

16. Sensor according to claim 15, characterized in that said multichannel structure is made in the form of a straight length of polycapillary tube.

17. Sensor according to claim 15, characterized in that said multichannel structure is made in the form of a curved length of polycapillary tube.

18. Sensor according to claim 15, characterized in that said multichannel structure is made as a length of polycapillary tube in the form of a tablet having length less than its transverse dimensions.

19. Sensor according to claim 6, characterized in that said organic substance forming one of the layers filling up microchannels is optically transparent or radiolucent, and said length of polycapillary tube is made with possibility of transporting, correspondingly, optical or X ray radiation.

20. Sensor according to claim 19, characterized in that said multichannel structure is made in the form of a straight length of polycapillary tube.

21. Sensor according to claim 19, characterized in that said multichannel structure is made in the form of a curved length of polycapillary tube.

22. Sensor according to claim 19, characterized in that said multichannel structure is made as a length of polycapillary tube in the form of a tablet having length less than its transverse dimensions.

23. Sensor according to claim 1, characterized in that said organic substance forming one of the layers filling up microchannels is optically transparent or radiolucent, and said length of polycapillary tube is made with possibility of transporting, correspondingly, optical or X ray radiation.

24. Sensor according to claim 23, characterized in that said multichannel structure is made in the form of a straight length of polycapillary tube.

25. Sensor according to claim 23, characterized in that said multichannel structure is made in the form of a curved length of polycapillary tube.

26. Sensor according to claim 23, characterized in that said multichannel structure is made as a length of polycapillary tube in the form of a tablet having length less than its transverse dimensions.

27. Sensor according to claim 2, characterized in that said organic substance forming one of the layers filling up microchannels is optically transparent or radiolucent, and said length of polycapillary tube is made with possibility of transporting, correspondingly, optical or X ray radiation.

28. Sensor according to claim 27, characterized in that said multichannel structure is made in the form of a straight length of polycapillary tube.

29. Sensor according to claim 27, characterized in that said multichannel structure is made in the form of a curved length of polycapillary tube.

30. Sensor according to claim 27, characterized in that said multichannel structure is made as a length of polycapillary tube in the form of a tablet having length less than its transverse dimensions.

* * * * *